United States Patent
Lachaine et al.

(10) Patent No.: US 7,672,705 B2
(45) Date of Patent: *Mar. 2, 2010

(54) WEIGHTED SURFACE-TO-SURFACE MAPPING

(75) Inventors: Martin Lachaine, Montreal (CA); Tony Falco, Montreal (CA)

(73) Assignee: Resonant Medical, Inc., Montreal, Quebec (CA)

( * ) Notice: Subject to any disclaimer, the term of this patent is extended or adjusted under 35 U.S.C. 154(b) by 797 days.

This patent is subject to a terminal disclaimer.

(21) Appl. No.: 10/894,392

(22) Filed: Jul. 19, 2004

(65) Prior Publication Data

US 2006/0036156 A1    Feb. 16, 2006

(51) Int. Cl.
    *A61B 5/05* (2006.01)
(52) U.S. Cl. .................................. 600/407; 382/128
(58) Field of Classification Search ................ 600/424, 600/415, 407, 425; 345/629, 639, 640; 382/128
    See application file for complete search history.

(56) References Cited

U.S. PATENT DOCUMENTS

| | | | |
|---|---|---|---|
| 3,082,322 A | 3/1963 | Koerner et al. ............ 250/61.5 |
| 3,777,124 A | 12/1973 | Pavkovich ................. 235/151 |
| 3,987,281 A | 10/1976 | Hodes ..................... 235/151.3 |
| 3,991,310 A | 11/1976 | Morrison .................... 250/312 |
| 5,099,846 A | 3/1992 | Hardy ...................... 128/653.1 |
| 5,107,839 A | 4/1992 | Houdek et al. ............ 128/653.1 |
| 5,207,223 A * | 5/1993 | Adler ......................... 600/427 |
| 5,291,889 A | 3/1994 | Kenet et al. .............. 128/653.1 |
| 5,301,674 A | 4/1994 | Erikson et al. ......... 128/661.01 |
| 5,379,642 A | 1/1995 | Reckwerdt et al. ............ 73/625 |
| 5,391,139 A | 2/1995 | Edmundson ................... 600/7 |
| 5,411,026 A | 5/1995 | Carol ..................... 128/660.03 |
| 5,442,675 A | 8/1995 | Swerdloff et al. ............. 378/65 |
| 5,447,154 A | 9/1995 | Cinquin et al. ........... 128/653.1 |
| 5,511,549 A | 4/1996 | Legg et al. ............... 128/653.1 |
| 5,531,227 A | 7/1996 | Schneider ................ 128/653.1 |
| 5,553,618 A * | 9/1996 | Suzuki et al. ............... 600/411 |
| 5,609,485 A | 3/1997 | Bergman et al. ............ 434/262 |
| 5,673,300 A | 9/1997 | Reckwerdt et al. ............ 378/65 |
| 5,690,108 A | 11/1997 | Chakeres ................. 128/653.1 |

(Continued)

FOREIGN PATENT DOCUMENTS

| | | |
|---|---|---|
| CA | 2 416 887 | 2/2002 |
| EP | 0 647 457 A1 | 10/1994 |
| EP | 0 647 457 B1 | 1/2002 |
| WO | 99/27839 | 6/1999 |
| WO | 99/27839 A2 | 6/1999 |
| WO | 99/27839 A3 | 6/1999 |
| WO | 03/076003 A2 | 9/2003 |
| WO | 03/076003 A3 | 9/2003 |

OTHER PUBLICATIONS

Besl et al., *A Method for Registration of 3d Shapes*, IEEE Transactions on Pattern Analysis and Machine Intelligence 14(2):239-256 (1992).

(Continued)

*Primary Examiner*—Brian Casler
*Assistant Examiner*—Jonathan G Cwern
(74) *Attorney, Agent, or Firm*—Goodwin Procter LLP

(57) ABSTRACT

A displacement of a lesion within a patient is determined for the purpose of administering radiation treatment by generating sets of surface elements from three-dimensional images of the lesion taken at different times. Weights are assigned to the surface elements, and based on weights and the proximity of corresponding elements in one set to elements in another set, a displacement is determined.

45 Claims, 8 Drawing Sheets

U.S. PATENT DOCUMENTS

| | | | |
|---|---|---|---|
| 5,715,166 | A | 2/1998 | Besl et al. ............... 364/474.24 |
| 5,754,623 | A | 5/1998 | Seki ............................ 378/65 |
| 5,810,007 | A | 9/1998 | Holupka et al. ......... 128/660.03 |
| 5,991,703 | A | 11/1999 | Kase .......................... 702/167 |
| 6,019,724 | A | 2/2000 | Gronninsaeter et al. ..... 600/439 |
| 6,106,470 | A | 8/2000 | Geiser et al. ................. 600/443 |
| 6,117,081 | A | 9/2000 | Jago et al. ..................... 600/443 |
| 6,119,033 | A * | 9/2000 | Spigelman et al. ........... 600/426 |
| 6,122,341 | A | 9/2000 | Butler et al. ................... 378/20 |
| 6,129,670 | A | 10/2000 | Burdette et al. .............. 600/427 |
| 6,285,805 | B1 | 9/2001 | Gueziec ........................ 382/299 |
| 6,292,578 | B1 | 9/2001 | Kalvin ......................... 382/131 |
| 6,307,914 | B1 * | 10/2001 | Kunieda et al. ................ 378/65 |
| 6,345,114 | B1 | 2/2002 | Mackie et al. .............. 382/132 |
| 6,359,959 | B1 | 3/2002 | Butler et al. ................... 378/20 |
| 6,385,286 | B1 | 5/2002 | Fitchard et al. ............... 378/65 |
| 6,385,288 | B1 * | 5/2002 | Kanematsu ................... 378/65 |
| 6,390,982 | B1 | 5/2002 | Bova et al. ................... 600/443 |
| 6,438,202 | B1 | 8/2002 | Olivera et al. ................. 378/65 |
| 6,516,046 | B1 * | 2/2003 | Frohlich et al. ............... 378/65 |
| 6,535,574 | B1 | 3/2003 | Collins et al. ................. 378/65 |
| 6,546,073 | B1 | 4/2003 | Lee ............................... 378/65 |
| 6,553,152 | B1 | 4/2003 | Miller et al. ................. 382/294 |
| 6,560,311 | B1 | 5/2003 | Shepard et al. ............... 378/65 |
| 6,591,127 | B1 | 7/2003 | McKinnon ................... 600/411 |
| 6,628,983 | B1 | 9/2003 | Gagnon ....................... 600/431 |
| 6,636,622 | B2 | 10/2003 | Mackie et al. .............. 382/132 |
| 6,661,870 | B2 | 12/2003 | Kapatoes et al. .............. 378/65 |
| 6,683,985 | B1 | 1/2004 | Kase et al. ................... 382/203 |
| 6,690,965 | B1 * | 2/2004 | Riaziat et al. ................ 600/428 |
| 6,750,873 | B1 * | 6/2004 | Bernardini et al. .......... 345/582 |
| 6,914,959 | B2 * | 7/2005 | Bailey et al. ................... 378/65 |
| 2001/0035871 | A1 | 11/2001 | Bieger et al. ................. 345/630 |
| 2001/0049475 | A1 * | 12/2001 | Bucholz et al. .............. 600/411 |
| 2002/0018588 | A1 | 2/2002 | Kusch ......................... 382/131 |
| 2002/0082494 | A1 | 6/2002 | Balloni et al. ................ 600/410 |
| 2002/0156375 | A1 | 10/2002 | Kessman et al. ............. 600/439 |
| 2002/0176541 | A1 | 11/2002 | Schubert et al. ............. 378/205 |
| 2002/0183610 | A1 | 12/2002 | Foley et al. .................. 600/407 |
| 2002/0188194 | A1 | 12/2002 | Cosman ....................... 600/426 |
| 2003/0018232 | A1 | 1/2003 | Elliott et al. ..................... 600/1 |
| 2003/0028401 | A1 * | 2/2003 | Kaufman et al. ................ 705/3 |
| 2003/0112922 | A1 | 6/2003 | Burdette et al. ............... 378/65 |
| 2004/0252870 | A1 * | 12/2004 | Reeves et al. ................ 382/128 |
| 2004/0260142 | A1 * | 12/2004 | Lovoi ............................ 600/1 |

OTHER PUBLICATIONS

Booth, *Modelling the impact of treatment uncertainties in radiotherapy*, University of Adelaide, Mar. 2002), Section 2.4 (http://thesis.library.adelaide.edu.au/uploads/approved/adtSUA20020816.175301/public/03chapter2.pdf.

Brujic et al., *Analysis of Free-Form Surface Registration*, International Conference on Image Processing, pp. 393-396 (1996).

Cuisenaire, O., http://www.tele.ucl.ac.be/PEOPLE/OC/these/node74.html, Posted Oct. 5, 1999, Downloaded from the Internet on Aug. 10, 2004.

Cuisenaire, O., http://www.tele.ucl.ac.be/PEOPLE/OC/these/node75.html, Posted Oct. 5, 1999, Downloaded from the Internet on Aug. 10, 2004.

Cuisenaire, O., http://www.tele.ucl.ac.be/PEOPLE/OC/these/node12.html, Posted Oct. 5, 1999, Downloaded from the Internet on Aug. 10, 2004.

Dubois et al. *Intraobserver and Interobserver Variability of MR Imaging- and CT-derived Prostate Volumes after Transperineal Interstitial Permanent Prostate Brachytherapy*, Radiology. 207(3):785-9 (1998).

Eggert et al., *Simultaneous Registration of Multiple Range Views for Reverse Engineering*. International Conference of Pattern Recognition, pp. 243-247 (1996).

Hanks, et al. , *Three Dimensional Conformal External Beam Treatment Of Prostate Cancer* http://prostate-help.org/download/pilgrim/10rad.pdf.

Hanks et al., *Clinical and Biochemical Evidence of Control of Prostate Cancer at 5 Years After External Beam Radiation* The Journal of Urology, vol. 154, 456-459 (1995).

Haralick et al., *Pose Estimation From Corresponding Data Point*, IEEE Transactions on Systems, Man, and Cybernetics, 19(6):1426-1446 (1989).

Hua et al., *Development of a Semi-Automatic Alignment Tool for Accelerated Localization of the Prostate*, Int. J. Radiation Oncology Biol. Phys., 55(3):811-823 (2003).

Jiang et al. *A New Approach to 3-d Registration of Multimodality Medical Images by Surface Matching*, SPIE vol. 1808 Visualization in Biomedical Computing, pp. 196-213 (1992).

Krempien et al., *Daily patient set-up control in radiation therapy by coded light projection*, 3 pages.

Michalski et al., *Three-Dimensional Conformal Radiation Therapy (3DCRT) for Prostate Cancer*, Radiation Oncology Center, Mallinckrodt Institute of Radiology, Washington University Medical Center, St. Louis, Missouri (1996) http://www.phoenix5.org/Infolink/Michalski/#3.

Paskalev et al., *Daily Target Localization for Prostate Patients based on 3-D Image Correlation*, Phys. Med. Biol., vol. 49, pp. 931-939 (2004).

Pennec et al,. *A Framework for Uncertainty and Validation of 3-D Registration Methods Based on Points and Frames*, International Journal of Computer Vision 25(3), 203-229 (1997).

Pito, *A Registration Aid*, International Conference on Recent Advanced in 3D Digital Imaging and Modelling, pp. 85-92 (1997).

Pollack et al., *Conventional vs. Conformal Radiotherapy for Prostate Cancer: Preliminary Results of Dosimetry and Acute Toxicity*, Int. J. Radiation Oncology Biol. Phys., 34(3):555-564.

Robb, *Three-Dimensional Visualization in Medicine and Biology*. Book Chapter in: Handbook of Medical Imaging: Processing and Analysis, ed. Isaac N. Bankman, Academic Press, San Diego, CA, Chapter 42, pp. 685-671 (2000).

Robinson, *Advances in Multi-Modal Data Analysis: The Analyze Software Environment*, http://www.ii.metu.edu.tr/~med-ii/makaleler/analyze_sw_enve.pdf, 5 pages. Downloaded on Aug. 10, 2004.

Soffen E.M. et al. *Conformal static field radiation therapy treatment of early prostate cancer versus non-conformal techniques: A reduction in acute morbidity*. Int J Radiat Oncol Biol Phys, 24: 485-488 (1992).

Thayananthan, A. et al., http://mi.eng.cam.ac.uk/~bdrs2/papers/thayananthan_cvpr03.pdf, pp. 1-8. Downloaded from the Internet on Aug. 10, 2004.

Tome et al. *Commissioning and Quality Assurance of an Optically Guided Three-dimensional Ultrasound Target Localization System for Radiotherapy*, Med. Phys., 29(8):1781-1788 (2002).

Zhang, *Iterative Point Matching for Registration of Free-Form Curves and Surfaces*, International Journal of Computer Vision, 13(2):119-152 (1994).

http://www.ucsf.edu/jpouliot/Course/chapter5.htm.

http://www.acmp.org/meetings/hershey_2001/highlights/benedict.pdf.

http://www.ucsf.edu/jpouliot/Course/Lesson22.htm.

http://www.gemedicalsystems.com/patient/see_treat/positioning.html.

http://www.emoryradiationoncology.org/high-technology.htm.

http://www.varian.com/pinf/imr000c.html.

http://www.ucsf.edu/jpouliot/Course/conformal_radiation_therapy.htm.

International Search Report for PCT/CA2005/001106 dated Nov. 15, 2005.

Written Opinion for PCT/CA2005/001106 dated Nov. 15, 2005.

International Preliminary Report on Patentability for International Application No. PCT/CA/2005/001106 dated Jan. 23, 2007.

Written Opinion of the International Searching Authority for International Application No. PCT/CA/2005/001106 dated Oct. 25, 2005.

Maurer C R et al., Registration of 3-D Images Using Weighted Geometrical Features, IEEE Transactions on Medical Imaging, IEEE Service Center, Piscataway, NJ, US vol. 15, No. 6, Dec. 1, 1996 (14 pages).

Zitova, B. et al., Image Registration Methods: A survey, Image and Vision Computing, Elsevier, Guildford, GB, vol. 21, No. 11, Oct. 1, 2003 (24 pages).

Christensen G. E., Inverse consistent registration with object boundary constraints, Biomedical Imaging: Macro to Nano, 2004, IEEE International Symposium on Arlington, VA, USA Apr. 15-18, 2004, Piscataway, NJ, USA, IEEE (18 pages).

Supplementary European Search Report for PCT/CA2005001106_RNM-003PC_dated Nov. 10, 2009, conducted by Examiner Miao Gao, 6 pages.

Leszczynski K W et al., "An Image Registration scheme applied to verification of radiation therapy" British Journal of Radiology British Inst. Radiol UK [Online] vol. 71, No. 844, Apr. 1998 (Apr. 1998), ISSN: 0007-1285, retrieved from the Internet: url:http://bjr.birjournals.org/cgi/reprint/71/844/413.pdf. [retrieved on Nov. 10, 2009].

* cited by examiner

WEIGHTED SURFACE-TO-SURFACE MAPPING

TECHNICAL FIELD

This invention relates to methods and systems for verifying anatomical features of a patient undergoing radiation therapy and, more particularly, to methods and systems for identifying common surface elements of anatomical elements common to multiple images.

BACKGROUND INFORMATION

Radiation-emitting devices are used for the treatment of cancerous tumors within patients. The primary goal of treating cancerous tumors with radiation therapy is the complete eradication of the cancerous cells, while the secondary goal is to avoid, to the maximum possible extent, damaging healthy tissue and organs in the vicinity of the tumor. Typically, a radiation therapy device includes a gantry that can be rotated around a horizontal axis of rotation during the delivery of a therapeutic treatment. A particle linear accelerator ("LINAC") is located within the gantry, and generates a high-energy radiation beam of therapy, such as an electron beam or photon (x-ray) beam. The patient is placed on a treatment table located at the isocenter of the gantry, and the radiation beam is directed towards the tumor or lesion to be treated.

Radiation therapy typically involves a planning stage and a treatment stage. Generally, the planning stage involves acquiring images of a lesion (using, for example an x-ray device) and subsequently using the image(s) to accurately measure the location, size, contour, and number of lesions to be treated. These are used to establish certain treatment plan parameters, such as an isocenter, beam angles, energy, aperture, dose distribution, and other parameters in an attempt to irradiate the lesion while minimizing damage to surrounding healthy tissue.

Determining the treatment parameters generally requires anatomical information such as the location of the tumor and surrounding critical organs. Generally, the patient is imaged with one or more imaging modalities using two-dimensional or three-dimensional imaging for planning purposes. A physician outlines the organs and volumes of interest, either manually or programmatically using one or more computer algorithms. The treatment plan is then designed to deliver the maximum radiation dose to the outlined target volume while minimizing the dose to surrounding healthy organs and normal tissue. The treatment plan can be designed manually by the user or by optimization algorithms.

Once a treatment plan is determined, the patient receives the radiation treatments during a number of sessions (fractions). Treatment often includes significant time lapses between individual fractions and can also span many weeks (e.g., once a day five days a week for four weeks.) Because organs can change location and/or shape from fraction to fraction, the original treatment plan may no longer be optimal. Three-dimensional imaging modalities that are able to discern soft-tissues are therefore used in the treatment room in order to detect and compensate for organ motion. Because of the time constraints imposed during the individual fractions, methods that provide fast, accurate, and reliable patient positioning data are of great benefit to a radiation technologist administering the radiation treatment.

SUMMARY OF THE INVENTION

The present invention provides systems and methods for determining patient positioning corrections to compensate for organ displacement and morphological change based on surface models derived from medical images taken at different times. In general, the invention relates to weighting one or more surface elements identified in at least two medical images taken at two or more different times and using various mapping techniques to determine changes in the location of the lesion or its shape. The present invention facilitates rapid and accurate treatment position adjustment just prior to treatment delivery while including important clinical and/or practical concerns not accounted for with other conventional methods.

In one aspect, a method for determining a displacement of a lesion within a patient undergoing radiation treatment includes generating a first set of surface elements from a first three-dimensional image of a portion of the lesion taken at a first time (such as during a treatment planning session); generating a second set of surface elements from a second three-dimensional image of a portion of the lesion taken at a second time (such as during a treatment delivery session); assigning weights to one or more of the elements; and determining a displacement of the lesion based on the proximity of surface elements to corresponding surface elements from the other image and the assigned weights.

In some embodiments, the method further includes adjusting the position of the patient (using, for example, rotational or translational movements) to compensate for the displacement and/or change in size, shape or orientation. The three-dimensional images can be generated using any suitable tomographic or other imaging modality, e.g., a CT scanner, a three-dimensional ultrasound device, a PET scanner, or an MRI device. In some embodiments, the three-dimensional images can be a prescription isodose surface. The surface elements can include triangles or other two-dimensional shapes, lines or points. The weight assigned to a surface element can be based on a degree of certainty that the surface element corresponds to a particular feature of the lesion, which in some cases can be an edge of the lesion; and/or on the clinical importance of an anatomical feature represented by the surface element and, in some embodiments, the proximity of an anatomical feature represented by the surface element to another anatomical structure of the patient. In some embodiments, the weights can be based on the density of the surface elements within a particular area of the image, and/or the area of the surface element itself.

In some embodiments, the method includes determining a mapping of one or more of the surface elements in the first set to corresponding surface elements in the second set. The mapping can be determined, for example, by minimizing the mean square distance between surface elements in the first set and corresponding surface elements in the second set. In embodiments where weights are assigned to elements in the first set and elements in the second set, the mapping can be determined, at least in part, based on a mathematical combination (such as the sums and or multiplicative products) of the weights assigned to pairs of corresponding elements.

In another aspect, a system for positioning a patient for the administration of radiation treatment of a lesion includes a register for establishing a first and second set of surface elements from two different three-dimensional images of at least a portion of the lesion taken at different times (such as a treatment planning session and a treatment delivery session); a module for assigning weights to at least one of the elements in the first set, or at least one of the elements in the second set, or elements in both sets; and a processor for determining a displacement of the lesion with respect to the different times and the assigned weights.

In some embodiments, the system further includes a controller adjusting the position of the patient to compensate for the displacement, and in some embodiments, the processor further determines a mapping of one or more of the surface elements in the first set to corresponding surface elements in the second set.

The foregoing and other objects, features and advantages of the present invention disclosed herein, as well as the invention itself, will be more fully understood from the following description of preferred embodiments and claims, when read together with the accompanying drawings.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Imaging is often used by oncologists in determining the treatment parameters of radiation therapy plans such that the prescribed radiation is sufficient to eliminate the cancerous cells and while conforming the shape of the dose distribution to a target volume to the greatest extent possible, thereby sparing healthy tissue from exposure to potentially harmful doses of radiation. To develop a preferred treatment plan, simulations can be performed to design a set of beams which accomplish this goal that calculate the dose at each point in the patient resulting from this set of beams. The dose distribution can be represented, for example, as isodose lines or as 3D isodose surfaces within the patient. The treatment goal is to encompass the lesion and an appropriate safety margin within the 100% isodose surface. The treatment plan is then administered, usually at a later date and over a period of weeks, based on the treatment parameters. One shortcoming of this approach is that the time lapse between treatment planning and treatment delivery allows for changes to the patient's anatomy, thereby potentially rendering the treatment plan sub-optimal. Changes such as lesion movement, growth, organ shifting, or other morphisms can cause healthy tissue to become subject to potentially harmful radiation, and cancerous tissue to extend beyond the boundaries of the original treatment plan.

Given the image of a lesion at time of treatment, an alternative to shifting the patient in a way as to make the lesion surface match with the planning surface is to shift the patient such that the lesion surface is correctly aligned with the prescription isodose surface.

Figure 1:
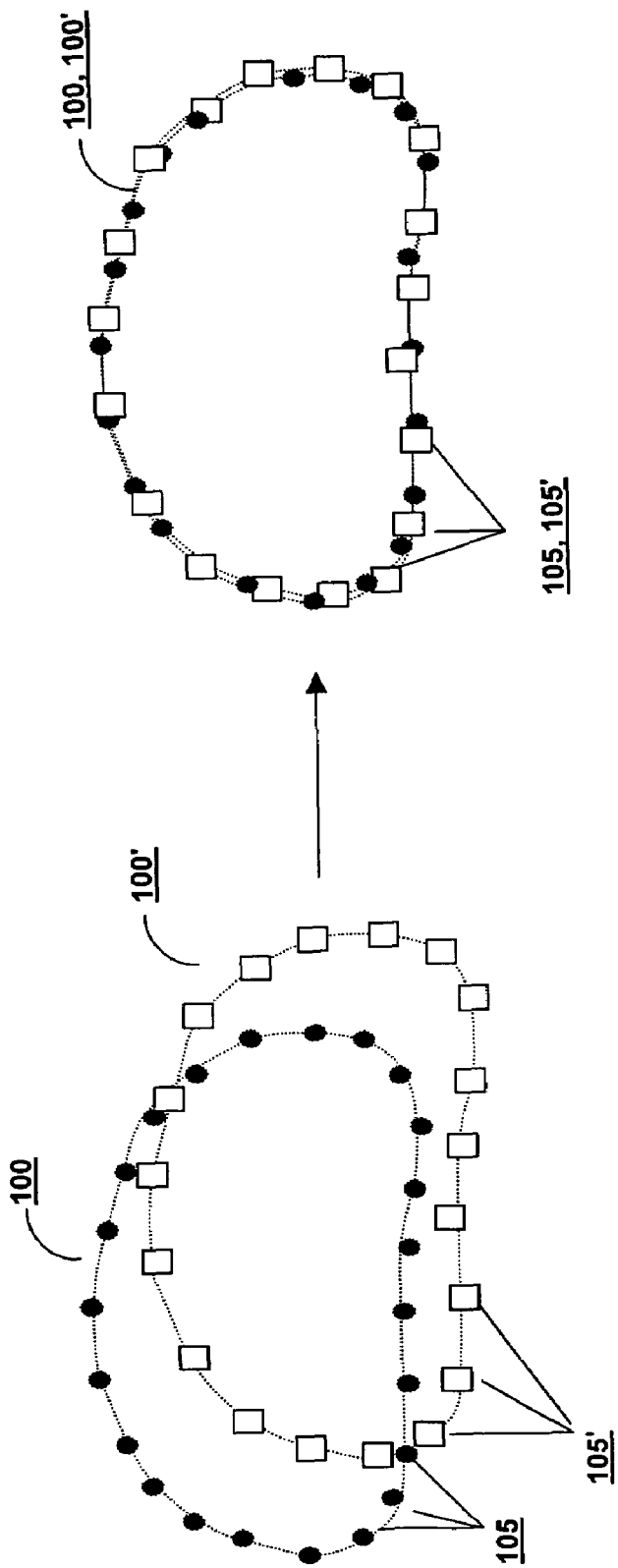
FIG. 1 schematically illustrates a mapping of surface elements of a lesion.

Referring to FIG. 1, a first image 100 and a second image 100' of a lesion are obtained at two different times—generally the first image 100 is obtained during a treatment planning stage, and the second image 100' during a treatment delivery stage. The images can be individual two-dimensional images, multiple two-dimensional sectional images or slices that collectively represent a volume and may be combined into a composite image, or three-dimensional images rendered programmatically or manually (or a combination). In some embodiments, one or more of the images can be a dose surface. The images can be obtained using devices such as CT scanners, ultrasound devices, MRI devices, PET scanners, and x-ray devices, as well as other imaging modalities commonly used throughout the art. The target of the radiation treatment may be a tumor or lesion independent of other organs, or a cancerous gland (such as the prostate) requiring treatment. The first image 100 is used by an oncologist, physician, or radiation technician to determine the location and shape of the lesion to be treated and to determine the parameters of the radiation treatment plan such as beam angle, beam shape, the number of beams needed to administer a sufficient dose to eradicate the target lesion, the dose level for each beams, and patient positioning. The second image 100' is obtained near the time the radiation is actually delivered to confirm the location and shape of the target lesion. However, due to the changes mentioned above, elements in the first image do not always appear in the same location or in the same shape in the second image. Therefore, it is necessary to match elements of each image to each other by identifying commonalties between the two images, 100, 100'.

To perform the matching, a set of elements 105 is identified in the first image 100 and a set of elements 105' is identified in the second image 100'. Using manual or programmatic techniques, the second set of elements 105' is mapped to corresponding elements 105 from the first image, and the "shift" necessary to move the two images such that the corresponding elements 105 and 105' are aligned is measured. This shift can then be translated into gross positional changes to be applied to the patient such that the radiation addresses the lesion without damaging surrounding tissue.

However, matching sets of surface elements is not always ideal. For example, the image from which the surface elements are being rendered is not always uniform—i.e., certain anatomical features in some areas of the image may be well-defined, whereas others may be blurry or hidden. Furthermore, certain healthy tissues that are overly sensitive to radiation (e.g., the rectum) may be located such that a very accurate boundary matching is required at certain points around the target lesion (e.g.: prostate), whereas other areas are less critical. Surface-matching algorithms such as those described herein account for such concerns as proximity of healthy overly sensitive structures, by weighting different surface elements accordingly.

During a treatment planning session, the organ or lesion surface is segmented into small components either manually, semi-automatically or automatically and a 3D planning surface image is generated. This surface can be described by points, line segments, a regular mesh, an analytic function, a set of triangles or other shapes, or any other surface representation. A second surface image (referred to as a "treatment surface") is generated at treatment time. In either or both images, some points on the surface may be known with more confidence than others due to, for example, poor edge information in some locations. In such a case, each surface element can be assigned a weight that indicates how confident either the user or the segmentation algorithm is that the surface element corresponds to a true border. In the extreme case, a weight of zero indicates that a given surface element is completely arbitrary since there is no reliable image data in that region.

Figure 2:
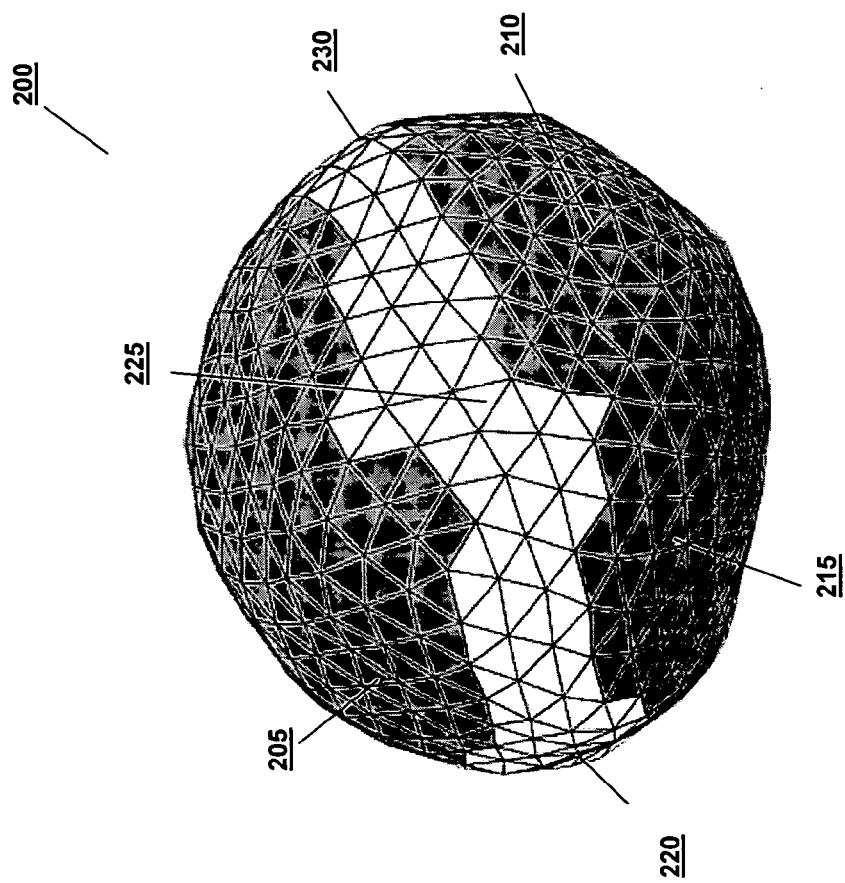
FIG. 2 schematically illustrates the surface of a lesion with certain elements weighted to influence a matching algorithm.

In FIG. 2, a lesion 200 to be treated using radiation has been segmented into numerous triangular sections, each representing a different surface element. Elements 205, 210, and 215 represent areas of the lesion that are weighted so as to be given greater consideration by the matching algorithm used to identify corresponding elements in a later image. Elements 220, 225, and 230 may also be considered during a matching process, but to discount any irregularities or compensate for unknowns in those areas, they are given a weighting lower than those assigned to elements 205, 210, and 215. In some instances, the imaging modality used to obtain the images may not provide complete representations of the lesion. However, incomplete images can still be used as input into a matching algorithm by weighting surface elements in non-imaged areas with a low, or even zero weight and assigning a greater weight to elements in areas accurately characterized in the image. As a result, the algorithm will find elements of the lesion in the second image that correspond to those elements that are substantially discernible or of greater importance in the first image.

The weighting of the individual elements can be based on the degree of certainty of surface points or elements identified in the image—i.e., parts of a lesion's surface which are known with a greater degree of certainty are assigned higher weights than those about which there is less certainty. The degree of certainty can, for example, represent the accuracy with which the image or portion thereof accurately corresponds to an actual anatomical feature of the patient; the level of confidence that the representation is located accurately with respect to other anatomical features, the patient, fiducial markers, or other positioning devices; or the degree of detail shown (and accurately represented) in the image. The weighting of surface elements can also be determined using gradient information obtained by analyzing the pixels of the image to determine closeness to a binary edge. Other reasons for assigning higher weights to certain surface elements with respect to others may be their clinical importance, such as their proximity to other critical organs or other highly-susceptible non-target tissues. For example, the posterior part of the prostate surface is close to the rectum and thus can be assigned a higher weight than elements on the rest of the prostate surface to ensure the prostate/rectal interface is correctly repositioned.

In addition to determining the weights based on anatomical features of the patient, the number and arrangement of the surface elements themselves can help determine the assigned weights. For example, the weights can be adjusted for the density of points within a particular region to reduce bias in the case of an unequal distribution of surface elements. Likewise, surface areas with only a few defined elements may be assigned reduced weights to reduce the effect of statistical outliers, to eliminate statistical noise, or to minimize damage to areas that have not been adequately characterized by imaging.

Figure 3:
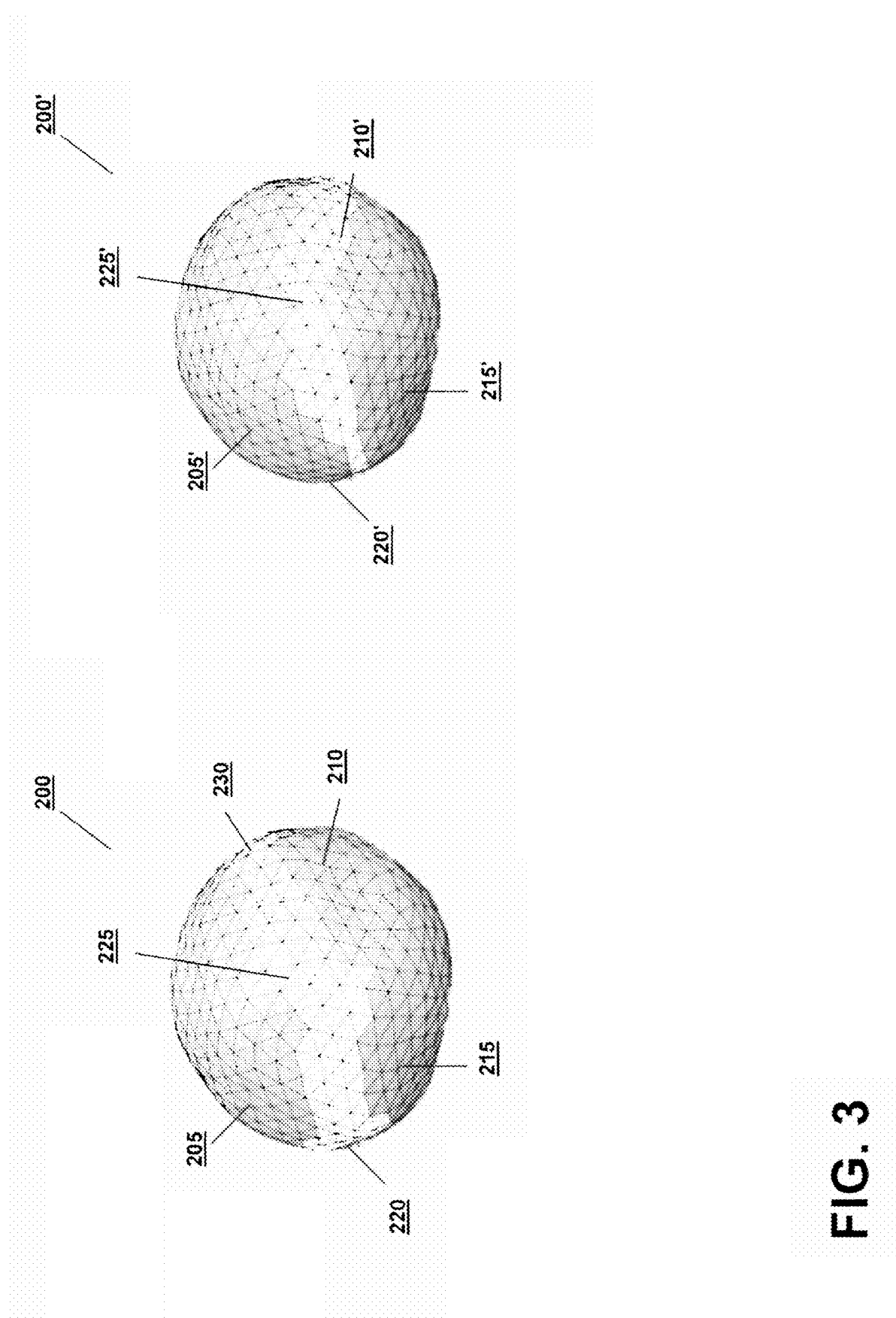
FIG. 3 schematically illustrates the surface of the lesion of FIG. 2 as extracted from two images take and different times.

FIG. 3 reproduces the first image 200 of the lesion shown in FIG. 2, and in addition, illustrates a second image 200' of the same lesion taken at a later time. The lesion in the second image is not only displaced, but due to differing image quality, the shaded regions of certainty are different in the two images. In particular, segment 210 which was certain in the first surface is uncertain in the second surface. Corresponding segments which have a high weight in both images, such as pairs 205, 205' and 215, 215' may be weighted heavily in the algorithm whereas segments which are weighted heavily in one surface but not the other, such as pairs 210, 210' and 220, 220' or in neither image such as 225, 225' may not be weighted heavily in the algorithm when determining the optimal shift such that images 200 and 200' are aligned properly.

In one example, two three-dimensional images are obtained, one during treatment planning and one in anticipation of treatment delivery. The images are segmented, either manually or programmatically using known segmentation or surface mesh techniques. Segments are assigned a certainty weight c indicating how certain it is that the segmented point corresponds to a true edge. In some embodiments, the certainty weight c is a real number, or in some cases limited to either 0 or 1 representing uncertain and certain boundaries, respectively. Other methods to generate certainty weights include, but are not limited to, using the magnitude of the gradient at the surface point, a closeness to another edge detection technique, or manual identification. The result of the segmentation is the generation of two surfaces, one at the time of treatment planning, $S_1$ and the other at treatment time, $S_2$. The surfaces can consist of, for example, points, lines, or other surface elements such as triangles (e.g., in a mesh). For ease of representation, surface elements are hereafter referred to as "points."

The set of 3D elements and certainty weights on $S_1$ are referred to as $\{r_j^{(1)}\}=\{x_j^{(1)},y_j^{(1)},z_j^{(1)},c_j^{(1)}\}$ and on $S_2$ as $\{r_i^{(2)}\}=\{x_i^{(2)},y_i^{(2)},z_i^{(2)},c_i^{(2)}\}$. The index i runs from 1 to the number of points M in $S_2$, and the index j runs from 1 to the number of points N in $S_1$. The terms x, y, z represent the 3D positional coordinates of each point and c refers to the certainty index assigned to that point. Either set of points can be downsampled to improve the speed of computation by removing excess points. The set of certainty indices of $S_2$ (or, in some cases $S_1$, or both) may be modified to account for the local density of elements in the case of surface points, or the area of the element in the case of a mesh, so that parts of surfaces with large density of elements are not overly weighted in the algorithm. As a result, the set of elements on $S_2$ are referred to as $\{r_i^{(2)}\}=\{x_i^{(2)},y_i^{(2)},z_i^{(2)},w_i^{(2)}\}$ where $w_i^{(2)}$ is the modified set of certainty indices $c_i^{(2)}$.

The shift $r_{shift}$ which minimizes least-square error between points on $S_1$ and $S_2$ is found, which includes the weights of the points on each surface. A method to determine this shift is to minimize the cost function given by $$C(r_{shift}) = \sum_i W_i \cdot \|r_1^{(2)} - r_{close}^{(2)}(r_i^{(2)} - r_{shift}, S_1) - r_{shift}\|^2 \quad (1)$$

where $r_{close}^{(1)}(r_i^{(2)}-r_{shift},S_1)$ refers to the point on $S_1$ which is the closest to the point $r_i^{(2)}-r_{shift}$, and the weights $W_i$ are defined as $$W_i = w_i^{(2)} \cdot c_{close}^{(1)}(r_i^{(2)}-r_{shift},S_i) \quad (2)$$

where $c_{close}^{(1)}(r_i^{(2)}-r_{shift},S_1)$ refers to the certainty weight of that closest point on $S_1$. One possible method of minimizing the cost of equation 1 includes the following steps:
1) Set $r_{shift}=(0,0,0)$
2) Calculate the set of closest points $r_{close}^{(1)}(r_i^{(2)}-r_{shift},S_1)$ in Eq. (1).
3) Calculate the cost $C(r_{shift})$ for this particular shift.

4) Is the cost below a threshold? If yes, stop and accept $r_{shift}$ as the optimal shift. If no, then update $r_{shift}$ to $r_{shift}+\Delta R$ where $\Delta R$ is an incremental update step.

5) return to step 2)

The shift vector $r_{shift}$ is updated by the update step $\Delta R$ until the cost function is a minimum. The result converges rapidly if $\Delta R$ is chosen such that:

$$\Delta R = \frac{1}{M}\sum_i W_i r_{close}^{(1)}(r_i^{(2)} - r_{shift}, S_1) - \frac{1}{N}\sum_i W_i r_i^{(2)}. \quad (3)$$

Rotations can also be introduced into the algorithm.

Figure 4A:
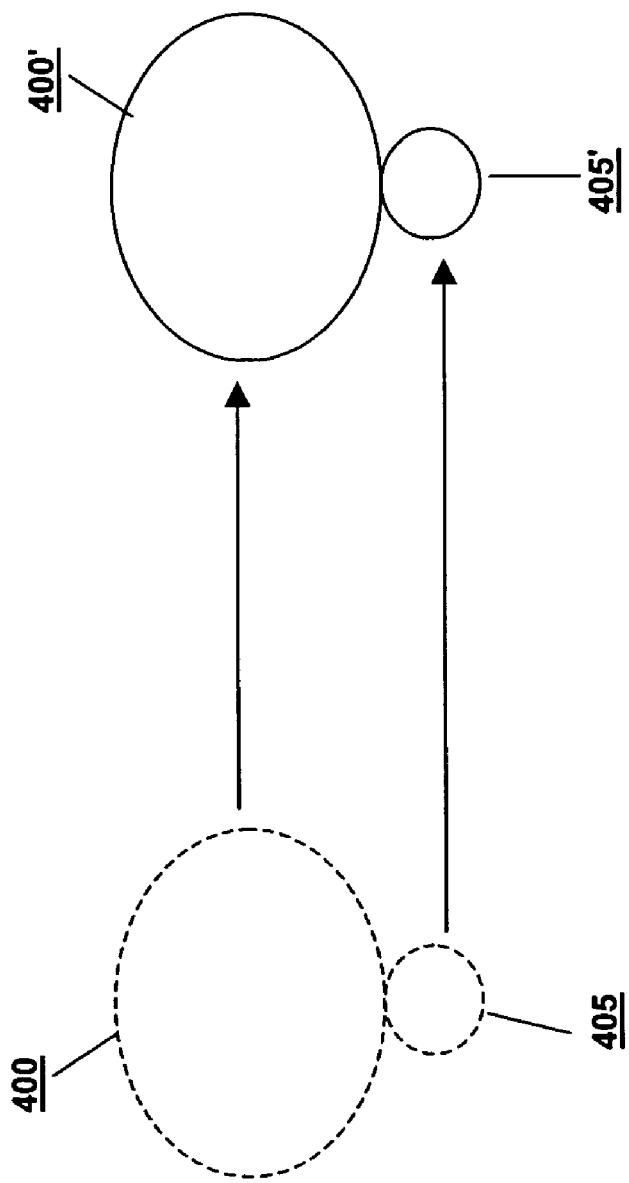
FIG. 4a schematically illustrates anatomical surface structures in a patient at both planning and treatment stages.
Figure 4B:
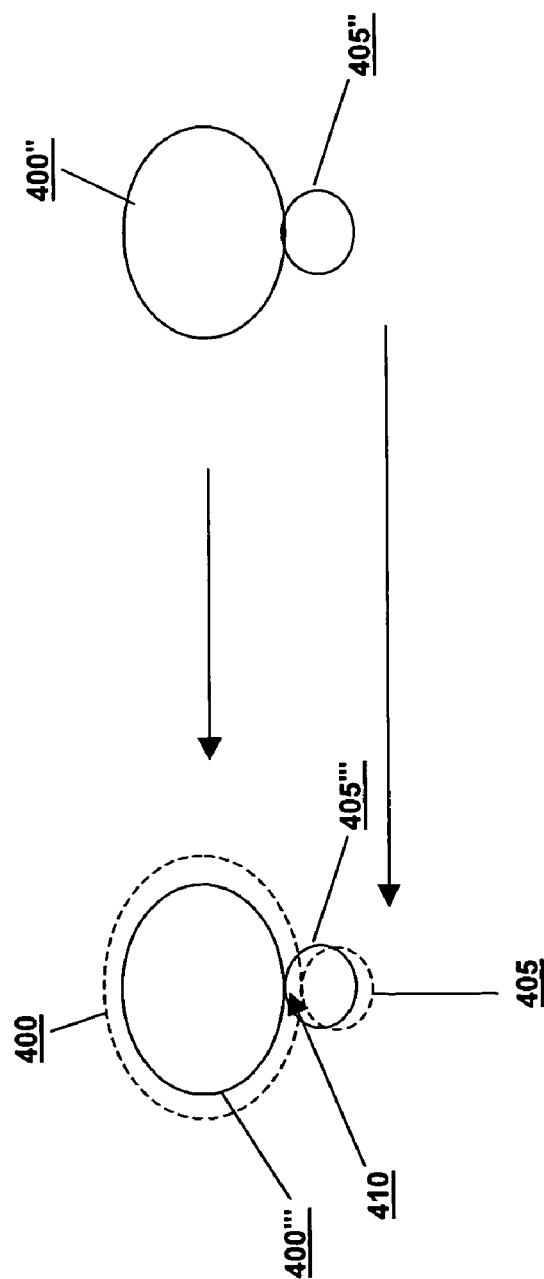
FIG. 4b schematically illustrates the anatomical surface structures of FIG. 4a at a first time, and the same features viewed in a second image taken at a second time after morphing has occurred.
Figure 4C:
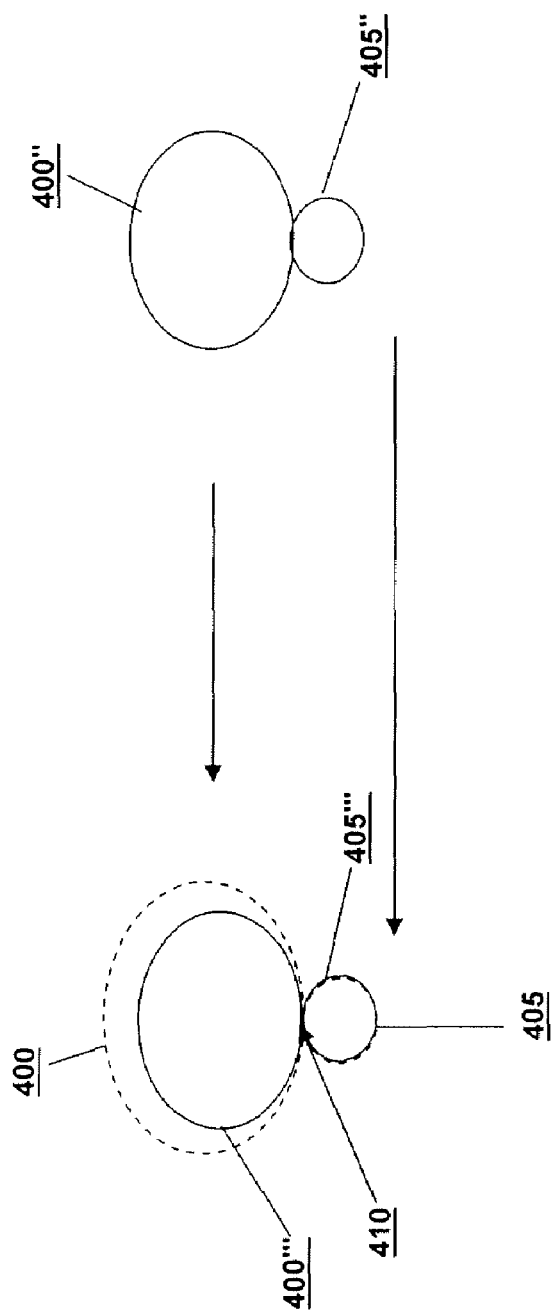
FIG. 4c schematically illustrates the anatomical surface structures of FIG. 4b where the structures are superimposed to illustrate a patient displacement accounting for lesion shifting.

FIGS. 4a, 4b, and 4c illustrate the results of using such a method to determine a positional shift given weighted surface elements. Referring to FIG. 4a, the prostate gland 400 and rectum 405 of a patient are shown as they exist at the time of treatment planning. Later, during treatment delivery, a second image is taken. In this instance, the prostate 400' and rectum 405' have shifted but there is no morphing. To correct for this change the organ simply needs to be shifted back into place using surface matching. FIG. 4b also shows the prostate 400 and rectum 405 in their original position and size as imaged during treatment planning, but in the interim between the planning session and the treatment delivery session, the prostate has not only been shifted but has also shrunk, as indicated at 400''. Because of the shrinking, the rectum has subsequently moved to position 405''. There is now more than one way to shift the organ back into place, as was the case in FIG. 4a. If, using one variation of our method described herein, all segments of the prostate are weighted equally in a surface matching algorithm, the prostate and rectum would be shifted to positions 400''' and 405''' respectively. In this case a segment 410 of the rectum is now within the original treatment area defined by the original size of the prostate 400. This is because every surface element, regardless of clarity or importance, has been treated equally during the matching process.

In contrast, FIG. 4c illustrates the results using another variation of the method described herein. The original prostate 400 and rectum 405 are identified, and the surface area along the boundary 410 between the prostate and rectum is weighted heavily to ensure a close match in that region in the surface matching calculation. Effecting the calculated shift results in the prostate and rectum assuming positions 400''' and 405''' respectively. As a result, the original treatment area 400 not only encompasses the entire reshaped prostate 400'', but avoids exposing the rectum 405 to potentially harmful radiation.

Figure 5:
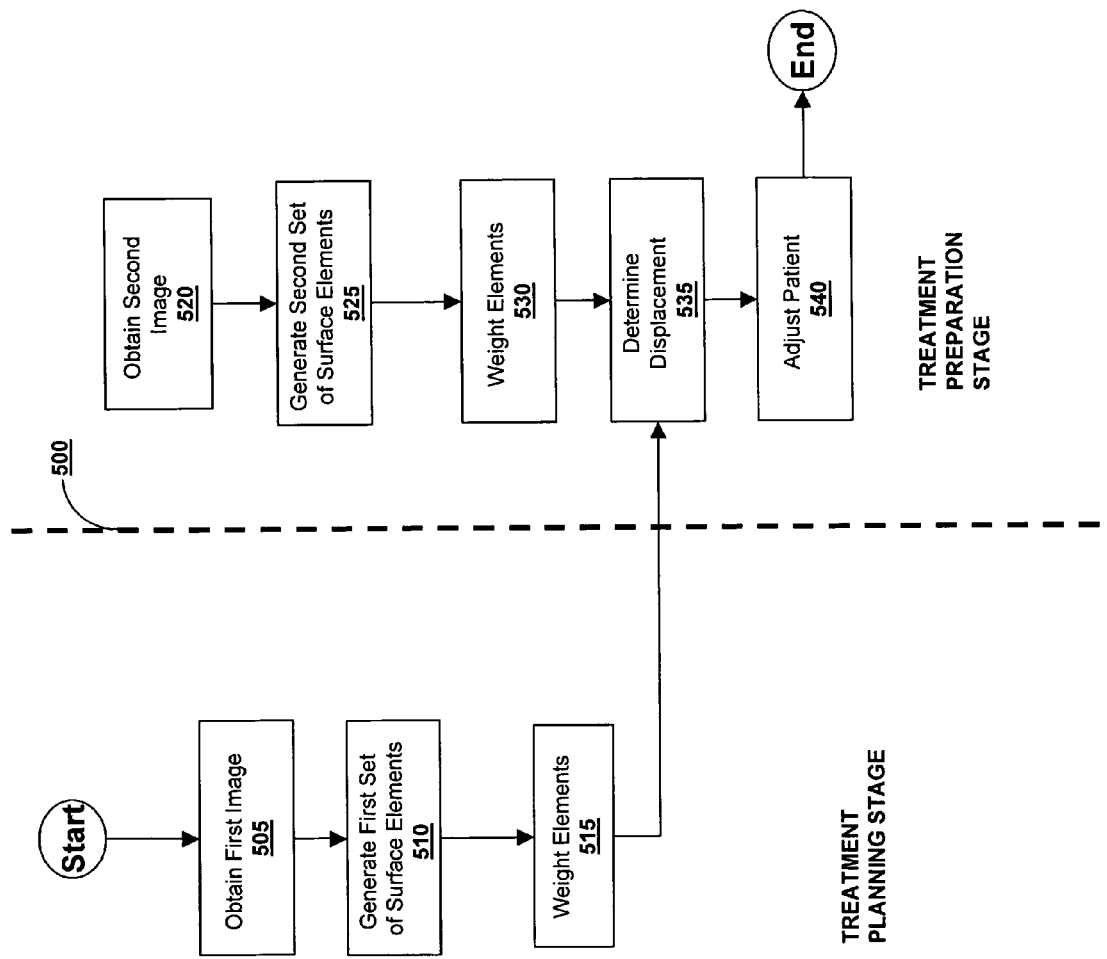
FIG. 5 is a flow diagram illustrating various embodiments of determining lesion displacement.

FIG. 5 illustrates various embodiments of a method of determining an appropriate adjustment to improve the delivery of radiation treatment to a patient. As described above, the process is typically divided into two phases: a treatment planning phase (corresponding to the steps to the left of the dashed line 500), during which an oncologist or similarly trained physician prepares a treatment plan for the administration of radiation to a cancerous lesion; and a treatment delivery phase (corresponding to the steps to the right of the dashed line 500) during which a radiology technician positions the patient within the gantry, makes any adjustments to the positioning based on lesion morphing or shifting, and administers the radiation according to the treatment plan. The treatment planning phase can occur substantially before the treatment delivery phase, or in some cases immediately preceding the treatment delivery phase, and may take place in the same room, or in some cases different rooms. As the time span increases between the phases, the target lesion has a greater opportunity to grow, change in morphology, and change its positioning with respect to surrounding normal tissue and healthy organs, resulting in a need for positional compensation.

As an initial step, a first image of the lesion and surrounding area is obtained (step 505) using any of the imaging modalities described above. In some instances, the image may not be a complete representation of the target lesion or surrounding organs, whereas in some instances the image can be a very accurate representation of the target area. From this first image, a set of surface elements is generated (step 510) representing one or more surface elements of the lesion and surrounding organs. The set of surface elements may include the entire three-dimensional surface, or in some cases where only a portion of the lesion has been accurately imaged, may only describe a portion of the lesion. One or more of the surface elements is weighted (step 515) based on one or in some cases a combination of the factors described above.

Subsequent to obtaining the treatment planning image, and in anticipation of a treatment delivery session, a second image of the target area is obtained (step 520). From this image, a second set of surface elements is generated (step 525) in a manner similar to the generation of the first set of surface elements. The surface elements are also assigned weights (step 530) relating to their intended influence on the matching algorithm. In some embodiments, weights may only be assigned to surface elements of the first set, and not of the second, or vice versa where one of the two images is more accurate that the other, or a significant amount of time has passed such that the second image is known to be a more accurate characterization of the current anatomical condition of the patient. Once surface elements have been matched using an algorithm such as that described above, the displacement can be determined (step 535) and the patient's position adjusted (step 540) accordingly.

The process of aligning surface elements of the two images involves shifting one of the images with respect to the other using any of a variety of image manipulation methods. An example of a typical shift maps the movement from the original position of the target structure to its pre-treatment delivery position (e.g., −4 pixels in the x direction and +8 pixels in the y direction). The shift can then be translated into a set of displacements for a patient support device, such as a treatment table of the LINAC, or the patient, just prior to or during treatment delivery. For example, a shift of (−4, +8) may translate into moving the treatment table 4 millimeters to the left and 8 millimeters up with respect to the gantry and radiation beam. Other shifts may require rotating the gantry, moving the patient, or some combination thereof.

Alternatively, a technician may use simulation techniques to directly manipulate the patient or patent support device while viewing the real-time images of the target area on a screen or monitor. In one embodiment, a technician can adjust the treatment table position with respect to the LINAC until a desired number of surface elements from the second image overlaps corresponding elements in the first image (or vice versa), or a threshold value is reached indicating a sufficient overlap, by manipulating an input device such as a joystick, keypad, or other input device. In another embodiment, the technician manually adjusts the position of the patient on a stationary treatment table until the desired position is reached. In some cases, the technician may employ a combination of both programmatic adjustments based on pre-determined alignment displacements and manual patient positioning techniques.

Figure 6:
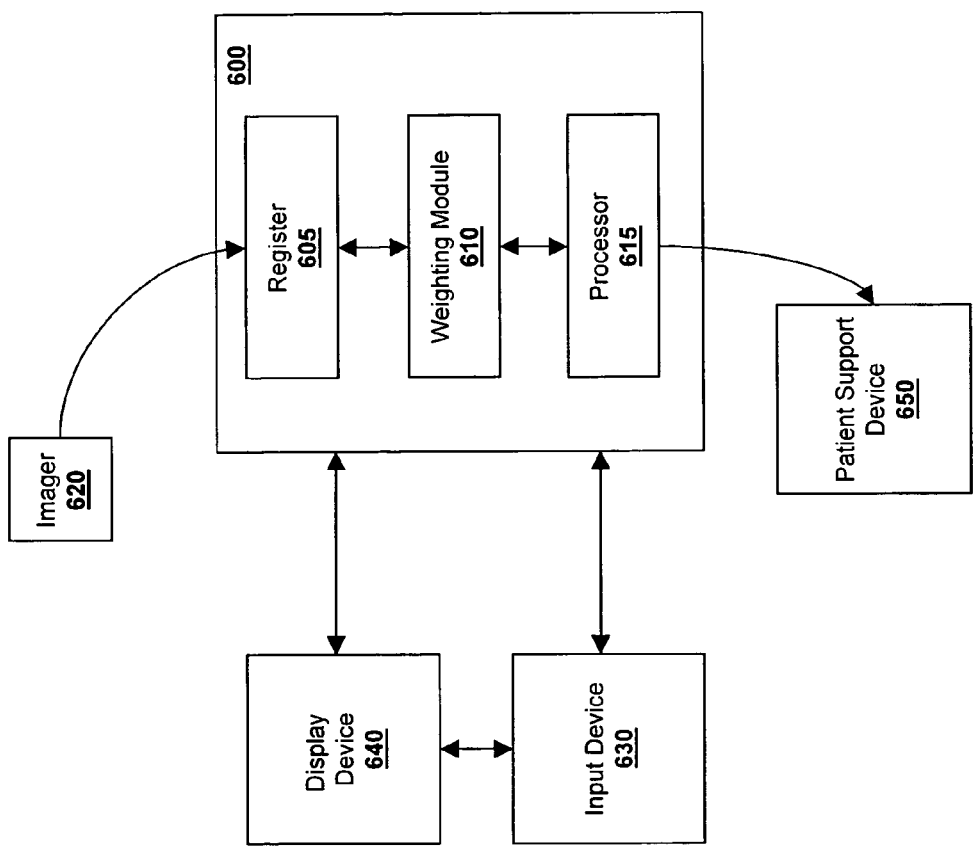
FIG. 6 is a schematic illustration of various embodiments of a system adapted to practice the methods of the present invention.

FIG. 6 schematically represents a hardware embodiment of the invention realized as a system 600 for positioning a patient in anticipation of the administration of radiation therapy. The system 600 comprises a register 605, a weighting module 610, and a processor 615.

The register 605, which may be any known organized data storage facility (e.g., partitions in RAM, etc.), receives images from an imager 620 such as an MRI, CT/PET scanner, ultrasound device, or x-ray device. The register 605 receives a first image from the imager 620 during or subsequent to a treatment planning session characterizing the target region at the time the treatment plan is determined. The register 605 receives a second image from the imager 620 during or just previous to a treatment delivery session characterizing the target region at the time of treatment. The imaging modalities used during the planning and the treatment stages can, in some embodiments, be different. In some embodiments, the images can be stored on a data storage device separate from the imager (e.g., a database, microfiche, etc.) and sent to the system 600. The register 605 may receive the images and beam shapes through conventional data ports and may also include circuitry for receiving analog image data and analog-to-digital conversion circuitry for digitizing the image data.

The register 605 then determines a set of surface elements from each image either programmatically, or based on some input from the user. In some cases, the determination of the surface elements from each of the two images is done simultaneously, whereas in other cases it is done upon receipt of the image from the imager 620. The register 605 then provides the images to the weighting module 610 that facilitates the assignment of weights to one or more surface elements generated from the first image, the second image, or both. The surface elements and weights can be determined programmatically, manually, or both. Where manual input and manipulation is used, the system 600 receives instructions from a user via an input device 630 such as a keyboard, a mouse, or other pointing device. Results of the weighting, manipulations, and alignments can also be viewed using a display device 640 such as a computer display screen or hand-held device. The set of surface elements and their associated weights are then sent to the processor 610 which, based on the proximity of the surface elements in each set and the assigned weights, determines the displacement of the lesion and any necessary changes to the patient's position to compensate for the displacement. The processor 615 translates displacements into instructions representing physical movements of a patient support device 650 and sends the instructions to the device 650 in order to adjust the position of the patient in accordance with the alignment calculations.

In some embodiments, the register 605, weighting module 610, and processor 615 may implement the functionality of the present invention in hardware or software, or a combination of both on a general-purpose computer. In addition, such a program may set aside portions of a computer's random access memory to provide control logic that affects one or more of the image manipulation, mapping, alignment, and support device control. In such an embodiment, the program may be written in any one of a number of high-level languages, such as FORTRAN, PASCAL, C, C++, C#, Java, Tcl, or BASIC. Further, the program can be written in a script, macro, or functionality embedded in commercially available software, such as EXCEL or VISUAL BASIC. Additionally, the software could be implemented in an assembly language directed to a microprocessor resident on a computer. For example, the software can be implemented in Intel 80x86 assembly language if it is configured to run on an IBM PC or PC clone. The software may be embedded on an article of manufacture including, but not limited to, "computer-readable program means" such as a floppy disk, a hard disk, an optical disk, a magnetic tape, a PROM, an EPROM, or CD-ROM.

While the invention has been particularly shown and described with reference to specific embodiments, it should be understood by those skilled in the area that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method for determining a shift for aligning temporally displaced images of a lesion entirely within a patient for the purpose of administering radiation treatment to the lesion, the method comprising the steps of:
    (a) generating a first set of one or more surface elements from a first three-dimensional image of at least a portion of the lesion taken at a first time;
    (b) generating a second set of one or more surface elements from a second three-dimensional image of at least a portion of the lesion taken at a second time;
    (c) assigning a weight to (i) one or more of the first set of surface elements, and (ii) one or more of the second set of surface elements, wherein the weights represent a certainty that a surface element represents an edge boundary of the lesion;
    (d) mapping one or more of the weighted surface elements of the first set to corresponding weighted surface elements in the second set;
    (e) determining a proximity between one or more of the mapped surface elements;
    (f) determining an optimal shift for aligning the lesion in the first and second images based on the proximities between, and weights attributed to, corresponding surface elements; and
    (g) adjusting the patient to obtain the optimal shift.

2. The method of claim 1 wherein the optimal shift comprises rotational movement.

3. The method of claim 1 wherein the optimal shift comprises translational movement.

4. The method of claim 1 wherein the first three-dimensional image is generated using one of a CT scanner, a three-dimensional ultrasound device, a PET scanner and an MRI.

5. The method of claim 1 wherein the second three-dimensional image is generated using one of a CT scanner, a three-dimensional ultrasound device, a PET scanner and an MRI.

6. The method of claim 1 wherein the first set of surface elements comprises at least one of the group consisting of points, triangles, and lines.

7. The method of claim 1 wherein the second set of surface elements comprises at least one of the group consisting of points, triangles, and lines.

8. The method of claim 1 wherein the weights assigned to one or more of the first set of surface elements are further based at least in part on a clinical importance of an anatomical feature represented by the one or more surface elements.

9. The method of claim 8 wherein the clinical importance of the one or more surface elements is based at least in part on the proximity of an anatomical feature represented by the surface element to another anatomical structure of the patient.

10. The method of claim 1 wherein the weights assigned to one or more of the first set of surface elements are further based at least in part on a density of the one or more surface elements within an area of the first image.

11. The method of claim 1 wherein the weights assigned to one or more of the first set of surface elements are further based at least in part on an area of the one or more surface elements.

12. The method of claim 1 wherein the weights assigned to one or more of the second set of surface elements are further based at least in part on a clinical importance of an anatomical feature represented by the one or more surface elements.

13. The method of claim 12 wherein the clinical importance of the one or more surface elements is based at least in part on the proximity of an anatomical feature represented by the surface element to another anatomical structure of the patient.

14. The method of claim 1 wherein the weights assigned to one or more of the second set of surface elements are further based at least in part on a density of the one or more surface elements within an area of the second image.

15. The method of claim 1 wherein the weights assigned to one or more of the second set of surface elements are further based at least in part on an area of the one or more surface elements.

16. The method of claim 1 wherein the mapping is determined by minimizing the mean square distance between surface elements in the first set and corresponding surface elements in the second set.

17. The method of claim 1 wherein the mapping is determined based at least in part on a mathematical combination of the weights assigned to pairs of the corresponding elements.

18. The method of claim 1 wherein the first time is substantially proximate to a treatment planning session.

19. The method of claim 1 wherein the second time is substantially proximate to a treatment session.

20. The method of claim 1 wherein the first three-dimensional image is a prescription isodose surface.

21. The method of claim 1 wherein the second three-dimensional image is a prescription isodose surface.

22. A system for determining a shift for aligning temporally displaced images of a lesion entirely within a patient for the purpose of administering radiation treatment to the lesion, the system comprising:
   (a) a register for storing (i) a first set of one or more surface elements from a first three-dimensional image of at least a portion of the lesion taken at a first time, and (ii) a second set of one or more surface elements from a second three-dimensional image of at least a portion of the lesion taken at a second time;
   (b) a module for assigning a weight to (i) one or more of the first set of surface elements, and (ii) one or more of the second set of surface elements, wherein the weights represent a certainty that a surface element represents an edge boundary of the lesion; and
   (c) a processor for mapping of one or more of the weighted surface elements of the first set to corresponding weighted surface elements in the second set, determining a proximity between one or more of the mapped_surface elements, and determining an optimal shift for aligning the lesion in the first and second images based on the proximities between, and weights attributed to, corresponding surface elements.

23. The system of claim 22 further comprising a controller for adjusting the position of the patient according to the optimal shift.

24. The system of claim 22 wherein the first three-dimensional image is generated using one of a CT scanner, a three-dimensional ultrasound device, a PET scanner and an MRI.

25. The system of claim 22 wherein the second three-dimensional image is generated using one of a CT scanner, a three-dimensional ultrasound device, a PET scanner and an MRI.

26. The system of claim 22 wherein the first set of surface elements comprises at least one of the group consisting of points, triangles, and lines.

27. The system of claim 22 wherein the second set of surface elements comprises at least one of the group consisting of points, triangles, and lines.

28. The system of claim 22 wherein the weights assigned to one or more of a subset of the first set of surface elements are further based at least in part on a clinical importance of an anatomical feature represented by the one or more surface elements.

29. The system of claim 28 wherein the clinical importance of the one or more surface elements is based at least in part on the proximity of an anatomical feature represented by the surface element to another anatomical structure of the patient.

30. The system of claim 22 wherein the weights assigned to one or more of a subset of the first set of surface elements are further based at least in part on a density of the one or more surface elements within an area of the first image.

31. The system of claim 22 wherein the weights assigned to one or more of a subset of the first set of surface elements are further based at least in part on a area of the one or more surface elements.

32. The system of claim 22 wherein the weights assigned to one or more of a subset of the second set of surface elements are further based at least in part on a clinical importance of an anatomical feature represented by the one or more surface elements.

33. The system of claim 32 wherein the clinical importance of the one or more surface elements is based at least in part on the proximity of an anatomical feature represented by the surface element to another anatomical structure of the patient.

34. The system of claim 22 wherein the weights assigned to one or more of a subset of the second set of surface elements are further based at least in part on a density of the one or more surface elements within an area of the second image.

35. The system of claim 22 wherein the weights assigned to one or more of a subset of the second set of surface elements are further based at least in part on an area of the one or more surface elements.

36. The system of claim 22 wherein the mapping is determined by minimizing the mean square distance between surface elements in the first set and the corresponding elements of the second set.

37. The system of claim 22 wherein the mapping is determined based at least in part on a mathematical combination of the weights assigned to pairs of the corresponding elements.

38. The system of claim 22 wherein the first time is substantially proximate to a treatment planning session.

39. The system of claim 22 wherein the second time is substantially proximate to a treatment session.

40. The system of claim 22 wherein the first three-dimensional image is a prescription isodose surface.

41. The system of claim 22 wherein the second three-dimensional image is a prescription isodose surface.

42. A system for determining a shift for aligning temporally displaced images of a lesion entirely within a patient for the purpose of administering radiation treatment to the lesion, the system comprising:
   (a) means for generating a first set of one or more surface elements from a first three-dimensional image of at least a portion of the lesion taken at a first time;

(b) means for generating a second set of one or more surface elements from a second three-dimensional image of at least a portion of the lesion taken at a second;
(c) means for assigning a weight to at least one of (i) one or more of the first set of surface elements, and (ii) one or more of the second set of surface elements, wherein the weights represent a certainty that a surface element represents an edge boundary of the lesion;
(d) means for mapping one or more of the weighted surface elements of the first set to corresponding weighted_surface elements in the second set;
(e) means for determining a proximity between one or more of the mapped weighted surface elements;
(f) means for determining an optimal shift for aligning the lesion in the first and second images based on the proximities between, and weights attributed to corresponding weighted surface elements; and
(g) means for adjusting a position of the patient to obtain the optimal shift.

43. The system of claim 42 wherein the mapping is determined by minimizing the mean square distance between the weighted surface elements in the first set and the weighted corresponding elements of the second set.

44. The system of claim 42 wherein the first time is substantially proximate to a treatment planning session.

45. The system of claim 42 wherein the second time is substantially proximate to a treatment session.

* * * * *